(12) United States Patent
Rayon et al.

(10) Patent No.: US 8,758,411 B1
(45) Date of Patent: Jun. 24, 2014

(54) IMPLANTS AND METHODS FOR TREATING SPINAL DISORDERS

(71) Applicant: NuVasive, Inc., San Diego, CA (US)

(72) Inventors: Enrique Rayon, Chula Vista, CA (US); Jennifer Jassawalla, San Diego, CA (US); Niall Casey, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/694,105

(22) Filed: Oct. 25, 2012

Related U.S. Application Data

(60) Provisional application No. 61/551,419, filed on Oct. 25, 2011.

(51) Int. Cl.
*A61B 17/70* (2006.01)

(52) U.S. Cl.
USPC ......................................................... 606/259

(58) Field of Classification Search
CPC ..................................................... A61B 17/70
USPC ................. 606/246, 250, 251, 259, 260, 261, 606/264–267, 270, 272, 277, 278, 279
See application file for complete search history.

(56) References Cited

U.S. PATENT DOCUMENTS

| | | | |
|---|---|---|---|
| 5,102,412 A | 4/1992 | Rogozinski | |
| 5,133,717 A | 7/1992 | Chopin | |
| 5,306,275 A | 4/1994 | Bryan | |
| 5,476,464 A | 12/1995 | Metz-Stavenhagen | |
| 5,562,663 A | 10/1996 | Wisnewski | |
| 5,776,135 A | 7/1998 | Errico | |
| 6,368,320 B1 | 4/2002 | Le Couedic | |
| 6,485,491 B1 | 11/2002 | Farris | |
| 6,554,832 B2 | 4/2003 | Shluzas | |
| 6,562,040 B1 | 5/2003 | Wagner | |
| 6,602,253 B2 | 8/2003 | Usher et al. | |
| 6,682,529 B2 | 1/2004 | Stahurski | |
| 6,755,830 B2 | 6/2004 | Minfelde | |
| 6,866,664 B2 | 3/2005 | Schär | |
| 7,090,674 B2 | 8/2006 | Doubler | |
| 7,166,109 B2 | 1/2007 | Biedermann | |
| 7,195,632 B2 | 3/2007 | Biedermann | |
| 7,276,069 B2 | 10/2007 | Biedermann | |
| 7,569,070 B2 | 8/2009 | Suzuki | |
| 7,572,278 B2 | 8/2009 | Suzuki | |
| 7,585,314 B2 | 9/2009 | Taylor | |
| 7,666,210 B2 | 2/2010 | Franck | |
| 7,691,131 B2 | 4/2010 | Graf | |

(Continued)

FOREIGN PATENT DOCUMENTS

| CN | 201930058 U | 8/2011 |
|---|---|---|
| FR | 2940757 A1 | 7/2010 |

(Continued)

*Primary Examiner* — Pedro Philogene
*Assistant Examiner* — David Comstock
(74) *Attorney, Agent, or Firm* — Jonathan Spangler; Rory Schermerhorn

(57) ABSTRACT

This application describes implants and methods for fixing two or more motion segments of a spine, particularly two or more motion segments located adjacent to a motion segment that was previously fixed during a prior surgery. An extension rod is described that attaches directly to the original fixation construct at one end. The opposing end of the extension rod is received and locked within a rod receptacle of a newly implanted pedicle screw at the adjacent level.

7 Claims, 14 Drawing Sheets

(56) References Cited

U.S. PATENT DOCUMENTS

| | | |
|---|---|---|
| 7,727,259 B2 | 6/2010 | Park |
| 7,850,715 B2 | 12/2010 | Banouskou |
| 7,922,746 B2 | 4/2011 | Miller |
| 7,942,902 B2 | 5/2011 | Schwab |
| 7,963,978 B2 | 6/2011 | Winslow |
| 7,993,371 B2 | 8/2011 | Farris |
| 8,021,399 B2 | 9/2011 | Ritland |
| 8,029,545 B2 | 10/2011 | Graf |
| 8,066,743 B2 | 11/2011 | Young |
| 8,080,037 B2 | 12/2011 | Butler |
| 8,097,022 B2 | 1/2012 | Marik |
| 8,114,141 B2 | 2/2012 | Appenzeller |
| 8,118,837 B2 | 2/2012 | Lemoine |
| 8,162,985 B2 | 4/2012 | Kim |
| 8,197,515 B2 | 6/2012 | Levy |
| 8,221,470 B2 | 7/2012 | Kumar |
| 8,236,028 B2 | 8/2012 | Kalfas |
| 8,262,700 B2 | 9/2012 | Cho |
| 8,262,701 B2 | 9/2012 | Rathbun |
| 8,298,266 B2 | 10/2012 | Miller |
| 8,337,527 B2 | 12/2012 | Hawkins |
| 8,337,532 B1 | 12/2012 | McLean |
| 8,343,166 B2 | 1/2013 | Maughan |
| 8,348,976 B2 | 1/2013 | Kohm |
| 8,366,746 B2 | 2/2013 | Kiester |
| 8,398,681 B2 | 3/2013 | Augostino |
| 8,518,085 B2 | 8/2013 | Winslow |
| 2004/0111088 A1 | 6/2004 | Picetti |
| 2004/0186473 A1 | 9/2004 | Cournoyer |
| 2004/0210216 A1 | 10/2004 | Farris |
| 2006/0079892 A1 | 4/2006 | Roychowdhury |
| 2006/0206114 A1 | 9/2006 | Ensign |
| 2007/0270818 A1 | 11/2007 | Rezach |
| 2008/0177323 A1* | 7/2008 | Null et al. .................... 606/267 |
| 2009/0036929 A1 | 2/2009 | Reglos |
| 2010/0063545 A1 | 3/2010 | Richelsoph |
| 2010/0217334 A1 | 8/2010 | Hawkes |
| 2010/0234892 A1 | 9/2010 | Mazda |
| 2010/0280552 A1 | 11/2010 | Lee |
| 2010/0298884 A1 | 11/2010 | Faizan |
| 2011/0034957 A1 | 2/2011 | Biedermann |
| 2011/0087287 A1 | 4/2011 | Reeder |
| 2011/0106164 A1 | 5/2011 | Wilcox |
| 2011/0106166 A1 | 5/2011 | Keyer |
| 2011/0106168 A1 | 5/2011 | Bucci |
| 2011/0110712 A1 | 5/2011 | Richelsoph |
| 2011/0118786 A1 | 5/2011 | Jang |
| 2011/0137345 A1 | 6/2011 | Stoll |
| 2011/0245883 A1 | 10/2011 | Dall |
| 2011/0270314 A1 | 11/2011 | Mueller |
| 2011/0270325 A1 | 11/2011 | Keyer |
| 2012/0101533 A1 | 4/2012 | Purcell |
| 2012/0179205 A1 | 7/2012 | Miller |
| 2012/0221053 A1 | 8/2012 | Copf |

FOREIGN PATENT DOCUMENTS

| | | |
|---|---|---|
| JP | 2011062407 A | 3/2011 |
| KR | 20030097249 A | 12/2003 |
| WO | WO-9909901 A1 | 3/1999 |
| WO | WO-2008027940 A1 | 3/2008 |
| WO | WO-2009022069 A2 | 2/2009 |
| WO | WO 2010056009 A2 * | 5/2010 |
| WO | WO-2010090428 A2 | 8/2010 |
| WO | WO-2012074803 A1 | 6/2012 |

* cited by examiner

IMPLANTS AND METHODS FOR TREATING SPINAL DISORDERS

CROSS-REFERENCES TO RELATED APPLICATIONS

This application is a non-provisional patent application claiming the benefit of priority from U.S. Provisional Patent Application Ser. No. 61/551,419, filed on Oct. 25, 2011, the entire contents of which is hereby expressly incorporated by reference into this disclosure as if set forth in its entirety herein.

FIELD

This application describes implants and methods for fixing two or more motion segments of a spine, particularly two or more motion segments located adjacent to a motion segment that was previously fixed during a prior surgery.

BACKGROUND

Spinal fusion is a procedure used to promote the fusion of two or more vertebrae in efforts to stabilize a damaged or deformed spine. Spinal fixation systems are often used during spinal fusion procedures to temporarily eliminate motion and secure a spinal motion segment in place until sufficient bone growth occurs to fuse the vertebrae together. One example of a commonly utilized fixation system is the pedicle screw construct. The pedicle screw construct typically includes some combination of pedicle screws anchored to the vertebrae of the motion segment(s) to be fixed and one or more fixation rods linking the pedicle screws. While spinal fusion procedures and pedicle screw fixation have a high rate of success, one potential complication of spinal fusion is adjacent segment disease. In adjacent segment disease, the fused motion segment can increase biomechanical stress on the unfused motion segments adjacent to the fused segment leading to changes in intradiscal pressure, hypermobility, and facet joint degeneration. Treatment for adjacent segment disease often involves reoperation on the spine to fuse the affected motion segments with the previously fused segments. Because instrumentation is already present (from the previous fusion procedure) in one of the vertebrae of the motion segment to be newly fused, the surgeon must remove the previously placed fixation rod, and sometimes one or more of the original pedicle screws, in order to create a new construct that spans the adjacent level segment to be fused. Removing this hardware requires exposing segments of the spine that might not otherwise have to be exposed to fuse the adjacent segment. The removal of hardware and the additional exposure it necessitates are undesirable in that it increases the technical demands on the surgeon, length of surgery time, potential for blood loss and other complications, and cost.

The implants and methods described herein are directed towards reducing the challenges associated with the treatment of adjacent segment disease.

BRIEF DESCRIPTION OF THE FIGURES

Many advantages of the present invention will be apparent to those skilled in the art with a reading of this specification in conjunction with the attached drawings, wherein like reference numerals are applied to like elements and wherein.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present application describes a fusion extension rod 10 that may be utilized to connect to a preexisting fixation construct and extend the construct to span additional levels. The extension rod can be connected to the existing construct without necessitating the removal of any component of the original construct. To accomplish this, the extension rod couples directly to the index rod (rod placed during the original fusion procedure), snakes around the adjacent index screw (screw placed in the original fusion procedure that is located closest to the adjacent segment to be fused), and aligns with and is coupled to the pedicle screw(s) newly implanted in the adjacent level vertebra.

Figure 1:
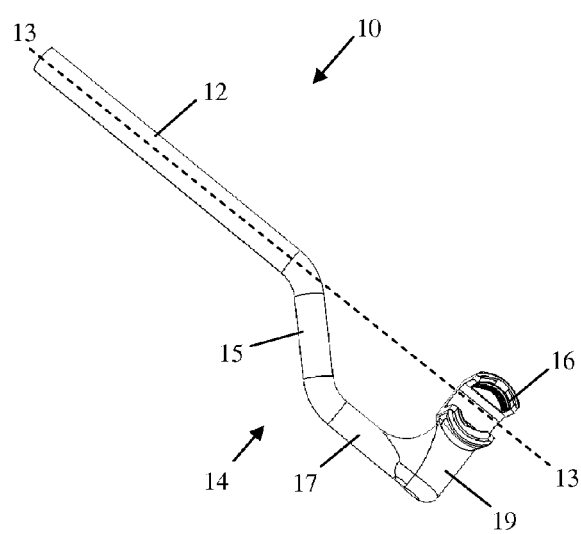
FIGS. 1-2 are perspective views of an extension rod for linking one or more pedicle screws to an existing spinal fixation construct, according to one example embodiment.
Figure 2:
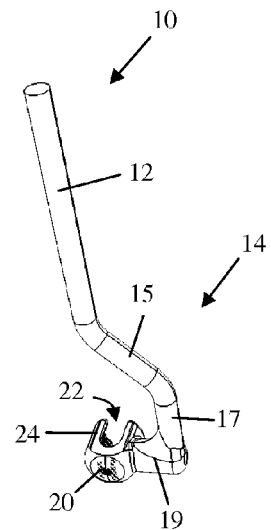
Figure 3:
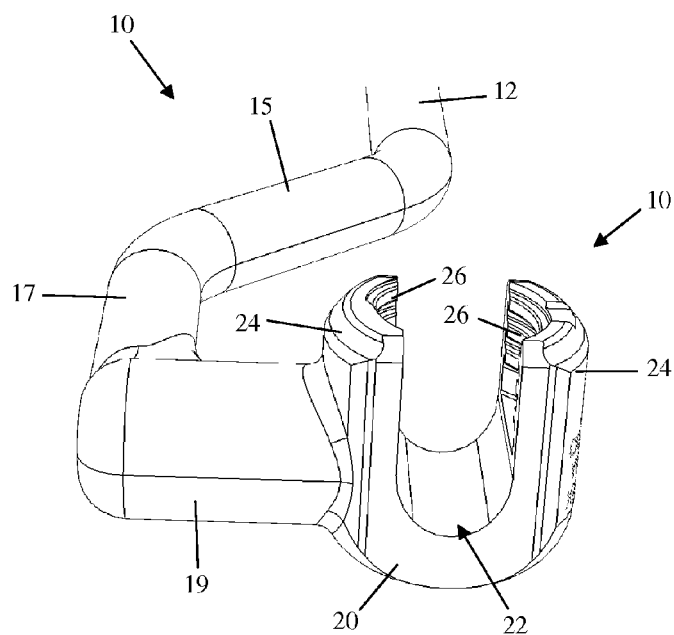
FIG. 3 is an enlarged view of a connecting element forming part of the extension rod of FIGS. 1-2.

FIGS. 1-3 illustrate a fusion extension rod 10 according to one example embodiment. The fusion extension rod 10 includes an extension segment 12 extending along a longitudinal axis 13, an offset segment 14, and a connecting element 16. At least the extension segment 12 is generally cylindrical and dimensioned to be received within a rod capturing component of the pedicle screw 40. The offset segment 14 can be further divided into three sub segments. The first sub segment 15 extends away from the extension segment 12 oblique to the longitudinal axis 13. The second sub segment 17 extends from the first sub segment 15 along an axis generally parallel to the longitudinal axis 13. The third sub segment 19 extends generally perpendicularly to the second sub segment 17 (and the longitudinal axis 13) and attaches to the connecting element 16 which includes a rod capture slot 26 in line with the longitudinal axis 13. Thus, the offset segment 14 creates an open space between the extension segment 12 and the connecting element 16 which can accommodate the adjacent index pedicle screw when the connecting element 16 is coupled to the index rod 28. Creating a space for the index pedicle screw allows the extended construct to be formed without increasing the height of the construct, as might happen if the extension rod were connected directly to or passed over the index pedicle screw 36.

The connecting element 16 has a base 20 with a pair of upstanding arms 24 extending therefrom and separated by a rod channel 22. The rod channel 22 is dimensioned to snugly receive the index rod 28 therein. The extension rod 10 may be constructed with a rod channel 22 having various dimensions adapted to receive one of several commonly utilized rod diameters (e.g. 4.5 mm, 4.75 mm, 5.5 mm, 6.35 mm, etc. . . . ) such that an extension rod 10 can be used to extend any previous fixation construct regardless of the particular specifications of the fixation system used in the original surgery. Likewise, the length of the extension segment 12 may be varied to account for different patient anatomy and/or multiple level connections. The arms 24 are equipped with a locking cap guide and advancement feature 26, such as by way of example, the helically wound flange feature disposed on the interior face of each arm 24. The guide and advancement feature 26 mates with a complementary guide and advancement feature formed on a locking cap 30 to lock the connecting element 16 to the index rod 28.

According to a preferred embodiment, the fusion extension rod 10 is made from a surgical-grade metal, including, but not necessarily limited to, titanium, stainless steel, and cobalt chrome. Alternatively, the fusion extension rod 10 could be composed of a carbon fiber reinforced plastic (CFRP). By way of example only, the plastic may be epoxy, polyester, vinyl ester, nylon, poly-ether-ketone-ketone (PEKK) poly-ether-ether-ketone (PEEK), or ceramic-reinforced PEEK.

Figure 4:
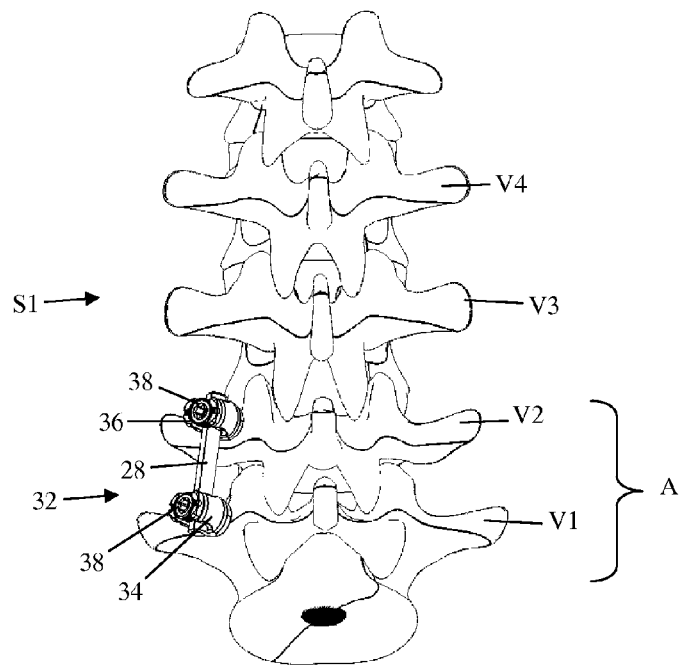
FIG. 4 is a posterior view of a lumbar spine with an existing (index) spinal fixation construct, including two pedicle screws and connecting rod, formed across a spinal motion segment, according to one example embodiment.
Figure 5:
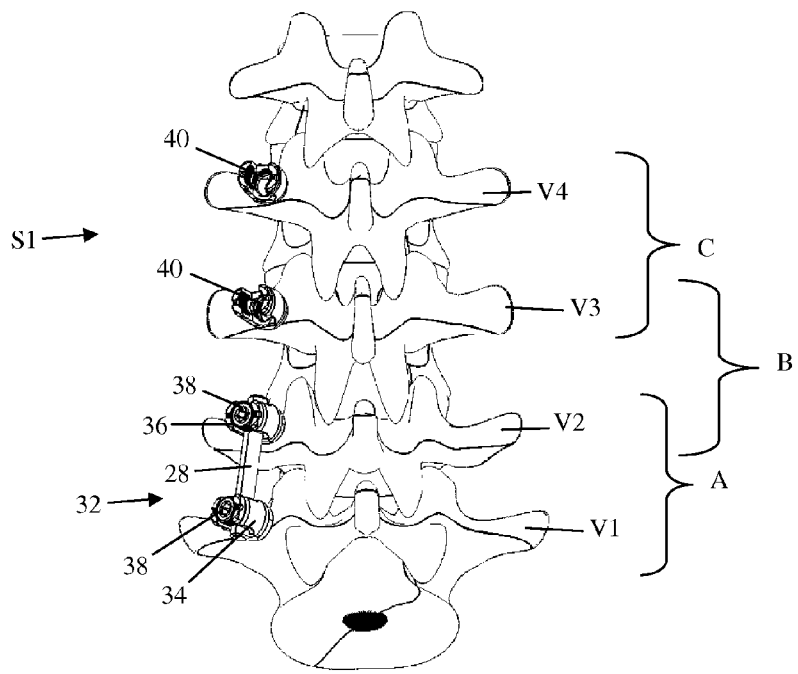
FIG. 5 is a posterior view of the lumbar spine of FIG. 4 with new pedicle screws engaged in the adjoining two segments above the index construct.
Figure 6:
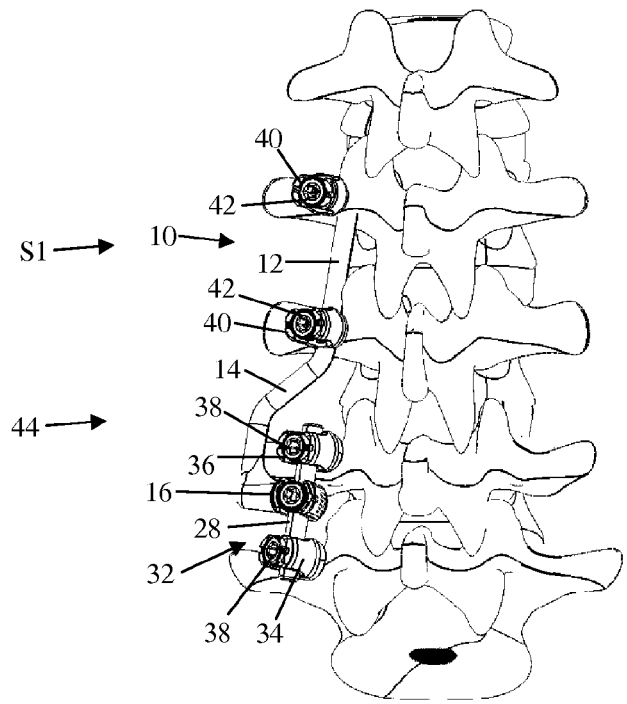
FIG. 6 is a posterior view of the lumbar spine of FIG. 5 with the extension connection of FIG. 1 in place and coupled to the index rod and new pedicle screws.

FIGS. 4-6 demonstrate the noteworthy steps used to extend an index fixation construct to span one or more adjacent segment levels during a subsequent surgery. FIG. 4 depicts a portion of a spine S1 on which an instrumented fusion was performed at motion segment A (vertebrae V1 and V2). The index fixation construct 32 implanted during the original fusion includes a distal index pedicle screw 34 anchored to vertebra V1 and an adjacent index pedicle screw 36 anchored to vertebra V2. Index rod 28 is seated within each of the index pedicle screws 34, 36 and locked in place with a locking cap 38. FIGS. 5-6 demonstrate how the extension rod 10 is employed to extend the fusion construct to adjacent levels without requiring the removal of any component of the index construct 32.

Figure 7:
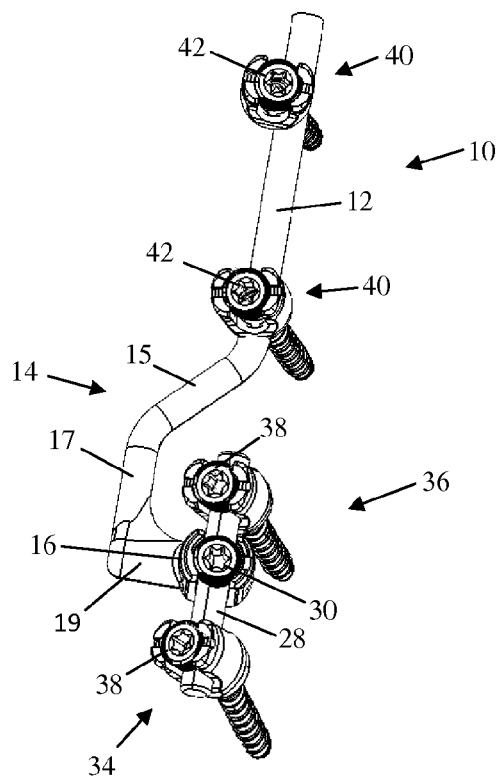
FIG. 7 is a perspective view of the spinal fixation construct of FIG. 6 with the lumbar spine removed.
Figure 8:
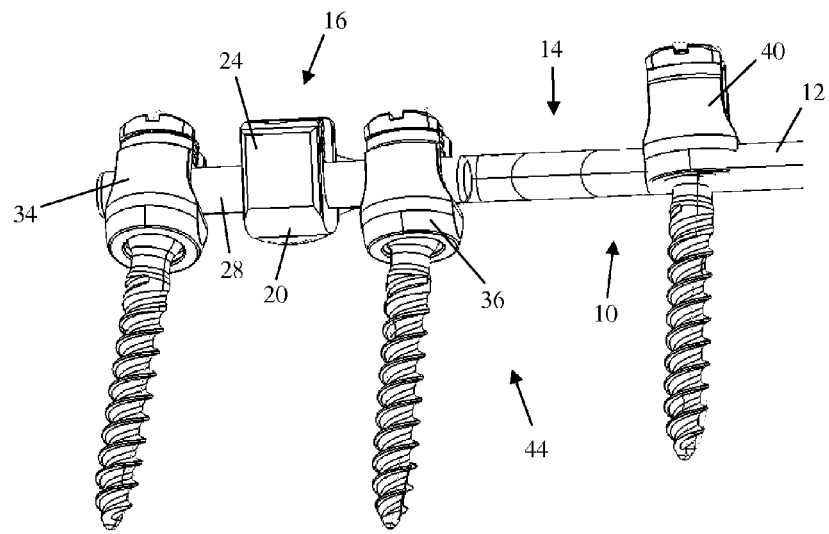
FIG. 8 is a medial side view of the spinal fixation construct of FIG. 7.
Figure 9:
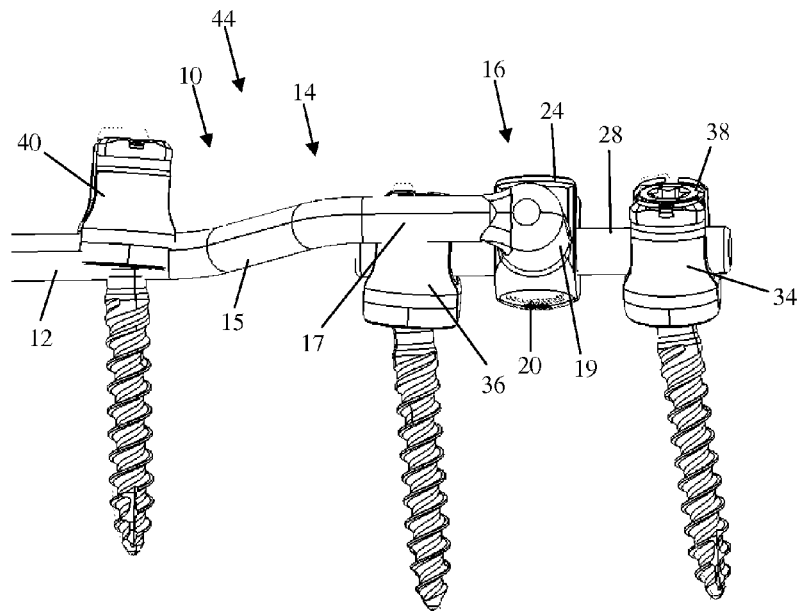
FIG. 9 is a lateral side view of the spinal fixation construct of FIG. 7.

FIG. 5 depicts the same spine S1 during a subsequent surgery when the fusion construct is to be extended to span motion segments B (vertebrae V2 and V3) and C (vertebrae V3 and V4). To accomplish this, exposure to spine S1 is performed sufficient to expose the pedicles of vertebrae V3 and V4 at one end and at least a portion of the index rod 28 at the other end. New pedicle screws 40 are anchored to vertebra V3 and vertebra V4. Next, as seen in FIG. 6, an appropriately sized extension rod 10 is selected such that the connecting element 16 can receive and lock the index rod 28 therein and the extension segment 12 can be received within the new pedicle screws 40. The extension rod 10 is advanced until the connecting element 16 engages the index rod 28. According to a preferred example, the extension rod 10 may be advanced with the rod channel 22 facing the top or side of the index rod 28. After capturing the index rod 28, the extension rod 10 may be rotated about the longitudinal axis 13 such that the rod channel rotates around the index rod 28 until a final desired position is achieved. Locking cap 30 is then engaged to lock the connecting element 16 to the index rod 28 and locking caps 42 are engaged to lock the extension rod 12 to the new pedicle screws 40 to complete the extended fixation construct 44. FIGS. 7-9 depict the extended rod fixation construct 44 without the spine S1 for illustrative purposes.

Figure 10:
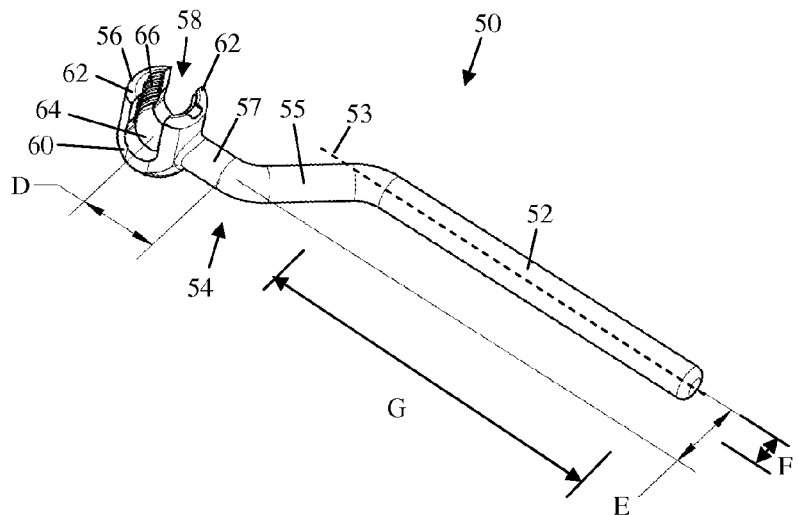
FIG. 10 is a perspective view of example embodiment of an extension rod for linking one or more pedicle screws to an existing spinal fixation construct, according to another example embodiment.

FIG. 10 depicts another example embodiment of a fusion extension rod 50. Whereas the extension rod 10 linked directly to the index rod 28 via connecting element 16, extension rod 50 utilizes any of a variety of connectors (examples of which are described below) to link to the index construct. Preferably, the additional connectors provide for polyaxial motion when joined with the extension rod 50, permitting motion in the sagittal and coronal planes (prior to locking the connection) to facilitate the connection with the new pedicle screws 40. The extension rod 50 includes an extension segment 52 extending along a longitudinal axis 53, an offset segment 54, and a connecting element 56. At least the extension segment 52 is generally cylindrical and dimensioned to be received within a rod capturing component of the new pedicle screw(s) 40. The offset segment 54 can be further divided into two sub segments. The first sub segment 55 extends away from the extension segment 52 oblique to the longitudinal axis 53. The second sub segment 57 extends from the first sub segment 55 along an axis generally parallel to the longitudinal axis 53. The second sub segment 57 attaches to the connecting element 56 which includes a capture slot 58 which is oriented perpendicularly to the longitudinal axis 53. The connecting element 56 has a base 60 with a pair of upstanding arms 62 extending therefrom and separated by capture slot 58. The capture slot 58 includes a spherical pocket 64 dimensioned to receive a spherical end 74 of a rod connector (e.g. rod connectors 76, 86, and 96). The arms 62 are equipped with a locking cap guide and advancement feature 66, such as by way of example, the helically wound flange feature disposed on the interior face of each arm 62. The guide and advancement feature 66 mates with a complementary guide and advancement feature formed on a locking cap 68 to lock the connecting element 56 to the index rod 28.

The extension rod 50 may be embodied in both left and right handed forms for application to either side of the side. It is also contemplated that the extension rod 50 may be provided with no offset segment 54 should it not be necessary to align the extension segment 52 with the index rod 28. Additionally, various dimensions of the extension rod 50 may be adjusted to provide a variety of extension rods that accommodate a wide variety of spinal environments. For example, the throat length D, offset E, extension segment diameter F, and extension segment lengths G may all be varied to achieve a plurality of extension rods 50 configured for different anatomical needs. According to a preferred embodiment, the fusion extension rod 50 is made from a surgical-grade metal, including, but not necessarily limited to, titanium, stainless steel, and cobalt chrome. Alternatively, the fusion extension rod 50 could be composed of a carbon fiber reinforced plastic (CFRP). By way of example only, the plastic may be epoxy, polyester, vinyl ester, nylon, poly-ether-ketone-ketone (PEKK) poly-ether-ether-ketone (PEEK), or ceramic-reinforced PEEK.

Figure 11:
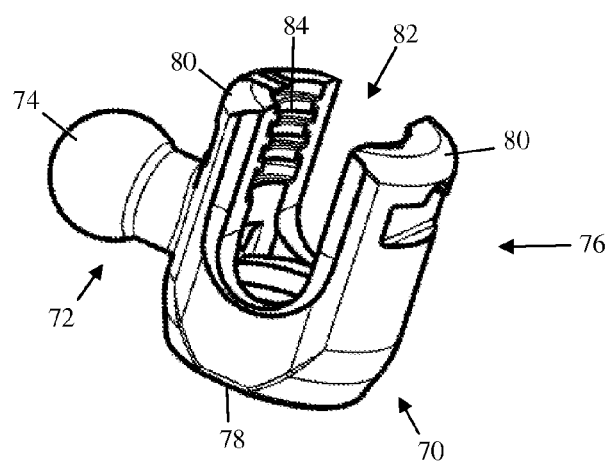
FIG. 11 is a perspective view of connector for use with the extension rod of FIG. 10, according to one example embodiment.
Figure 12:
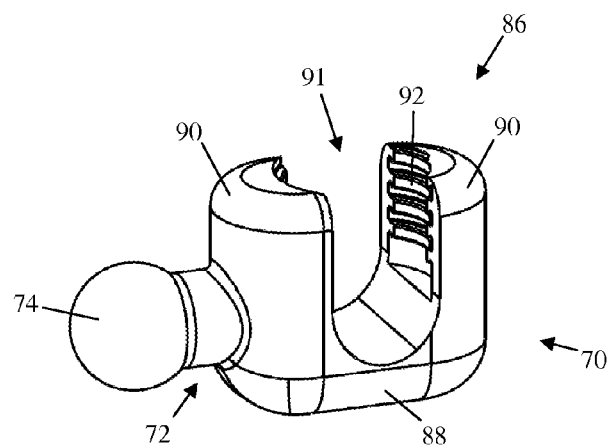
FIG. 12 perspective view of connector for use with the extension rod of FIG. 10, according to a second example embodiment.
Figure 13:
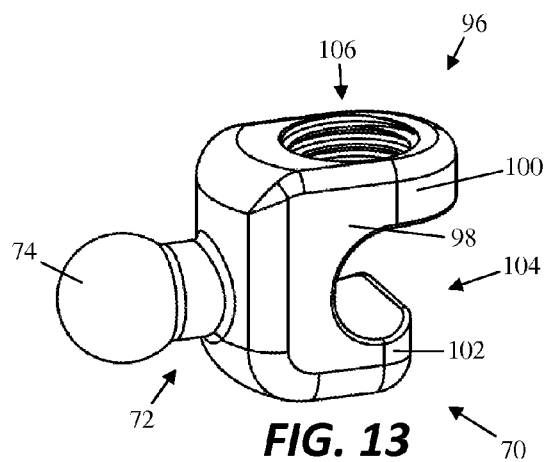
FIG. 13 is a perspective view of connector for use with the extension rod of FIG. 10, according to a third example embodiment.

FIGS. 11-13 illustrate different example embodiments (e.g. prophylactic tulip 76, open top connector 86, and open side connector 96) of connectors for use with the extension rod 50. Each of the various embodiments includes a rod connector body 70 and an extension arm 72 with a spherical end 74 extending from the connector body 70. When the rod connector is coupled to the index construct and the extension rod 50 is coupled to the rod connector (via sphere end 74) construct, the offset segment 54 provides accommodation for the index pedicle screw while the extension segment 52 aligns with rod and is coupled to the index rod 28. The spherical joint formed between the sphere end 74 and spherical pocket 64 allows motion in the sagittal and coronal planes (prior to locking the connection) to help position and properly seat the extension segment 52 in the new pedicle screws new pedicle screws 40.

FIG. 11 illustrates a first example connector in the form of prophylactic tulip connector 76. The prophylactic tulip connector 76 is considered a prophylactic because it is implanted as a part of the initial or index construct, as initial pedicle screw 36, during the original surgery. This may be done as a precautionary measure for patients exhibiting a strong potential for adjacent level segment failure. The prophylactic tulip connector 76 includes the rod connector body 70 and extension arm 72, as previously described. The tulip connector may be preassembled with the anchor portion of the pedicle screw or assembled in situ via any number of configurations commonly known in the art. The rod connector body 70 includes a base 78 with a pair of upstanding arms 80 extending therefrom and separated by rod capture slot 82. The arms 80 are equipped with a locking cap guide and advancement feature 84, such as by way of example, the helically wound flange feature disposed on the interior face of each arm 80. The guide and advancement feature 84 mates with a complementary guide and advancement feature formed on a locking cap 38 to lock the index rod 28 in the tulip 76 during the initial surgery. When the index screw 36 includes prophylactic tulip connector 76, the screw is implanted with the extension arm 72 positioned generally perpendicular to the axis of the index rod. During the subsequent surgery at least the extension arm 72 is exposed and any tissue surrounding the arm is removed. The connecting element 56 of the extension rod 50 is coupled to the sphere end 74 and the extension segment 12 is coupled to the new pedicle screw(s) 40.

FIG. 12 illustrates an open top connector 86. The open top connector 86 is configured to be coupled to the index rod 28 during the subsequent surgery (similar to the connecting element 16 of extension rod 10), and is considered non-prophylactic. The rod connector body 70 of open top connector body 86 includes a base 88 with a pair of upstanding arms 90 extending therefrom and separated by rod capture slot 91. The arms 90 are equipped with a locking cap guide and advancement feature 92, such as by way of example, the helically wound flange feature disposed on the interior face of each arm 90. The guide and advancement feature 92 mates with a complementary guide and advancement feature formed on a locking cap 94 to lock connector body to the index rod 28. The connecting element 56 of the extension rod 50 is coupled to the sphere end 74 and the extension segment 12 is coupled to the new pedicle screw(s) 40.

FIG. 13 illustrates an open side connector 96. The open side connector 96 is configured to be coupled to the index rod 28 during the subsequent surgery and is considered non-prophylactic. The rod connector body 70 of open top connector body 96 includes a base 98 with a pair of horizontally extending arms including top arm 100 and bottom arm 102 separated by rod slot 104. The top arm 100 includes a locking cap guide and advancement feature, for example, threaded aperture 106 which opens into the rod slot 104. The guide and advancement feature 106 mates with a complementary guide and advancement feature formed on a locking cap 108 to lock connector body to the index rod 28. The connecting element 56 of the extension rod 50 is coupled to the sphere end 74 and the extension segment 12 is coupled to the new pedicle screw(s) 40. The open side loading connector is advantageous in that the rod 28 can be coupled without having to fully pass the connector body under the rod.

Figure 14:
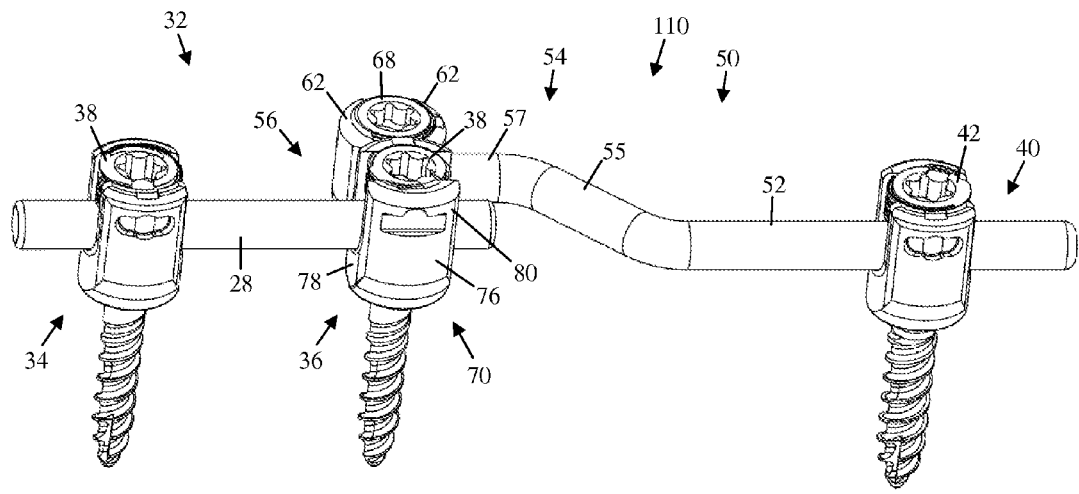
FIG. 14 is a perspective view of an extended spinal fixation construct with the extension rod of FIG. 10 and the connector of FIG. 11.
Figure 15:
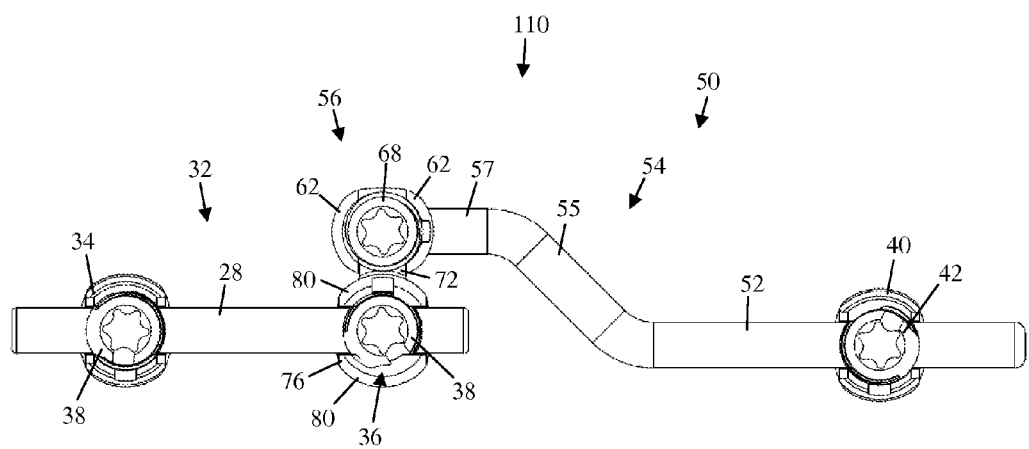
FIG. 15 is a top view of an extended spinal fixation construct with the extension rod of FIG. 10 and the connector of FIG. 11.
Figure 16:
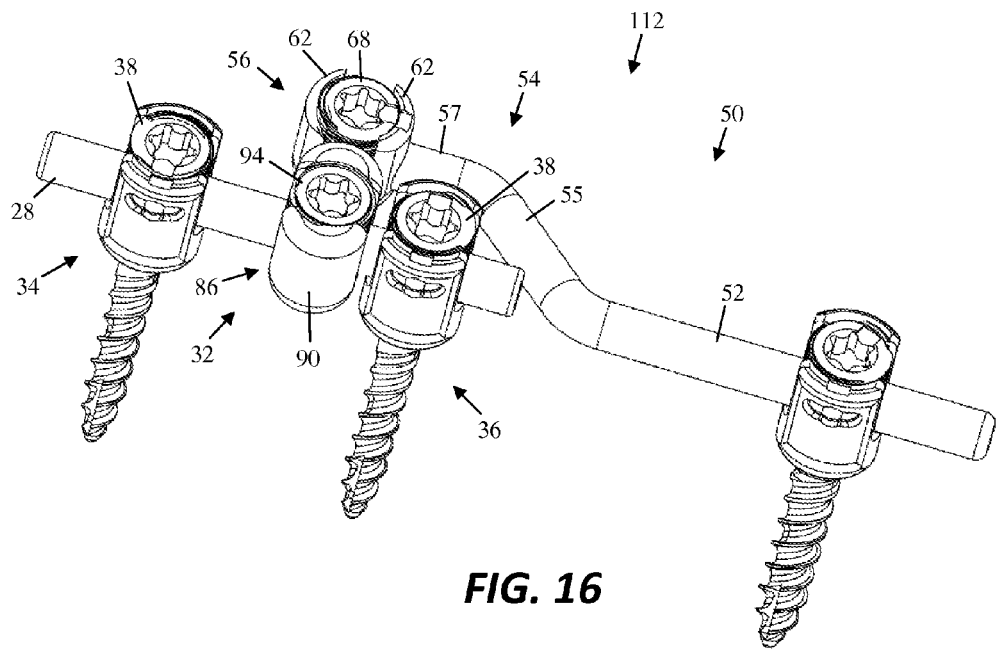
FIG. 16 is a perspective view of an extended spinal fixation construct with the extension rod of FIG. 10 and the connector of FIG. 12.
Figure 17:
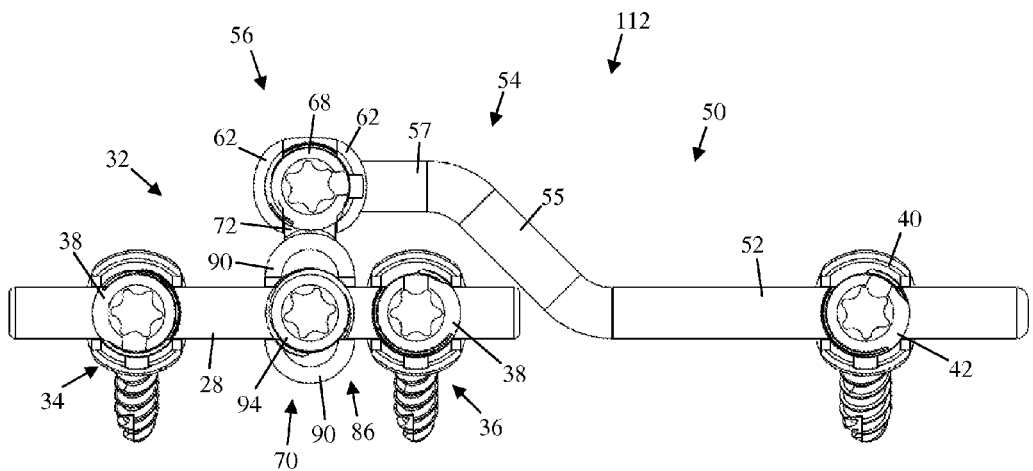
FIG. 17 is a top view of an extended spinal fixation construct with the extension rod of FIG. 10 and the connector of FIG. 12.
Figure 18:
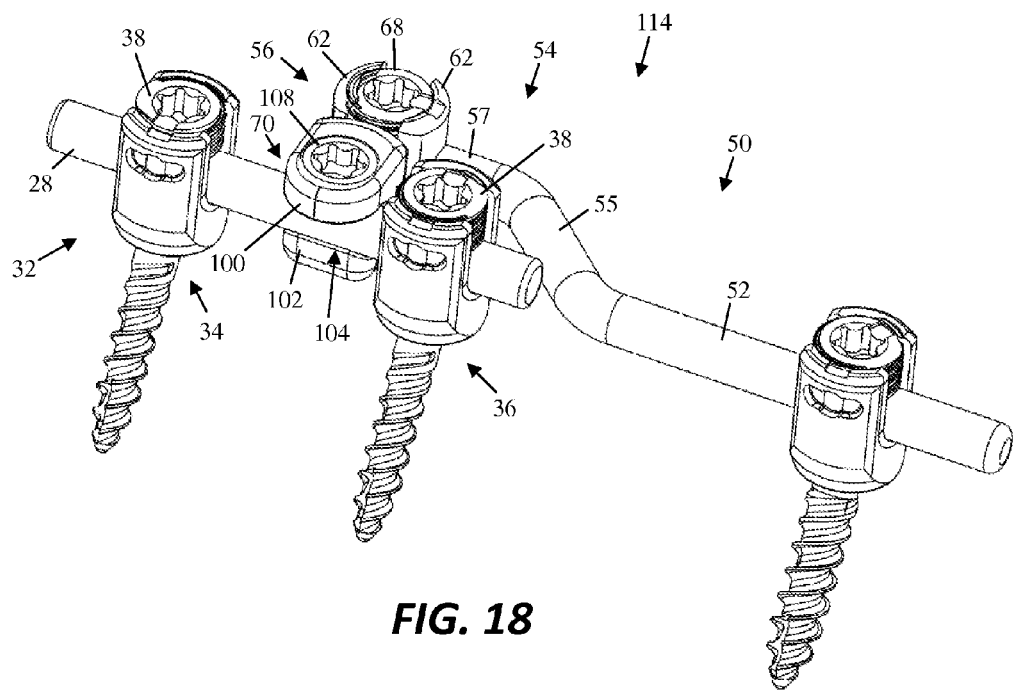
FIG. 18 is a perspective view of an extended spinal fixation construct with the extension rod of FIG. 10 and the connector of FIG. 13.
Figure 19:
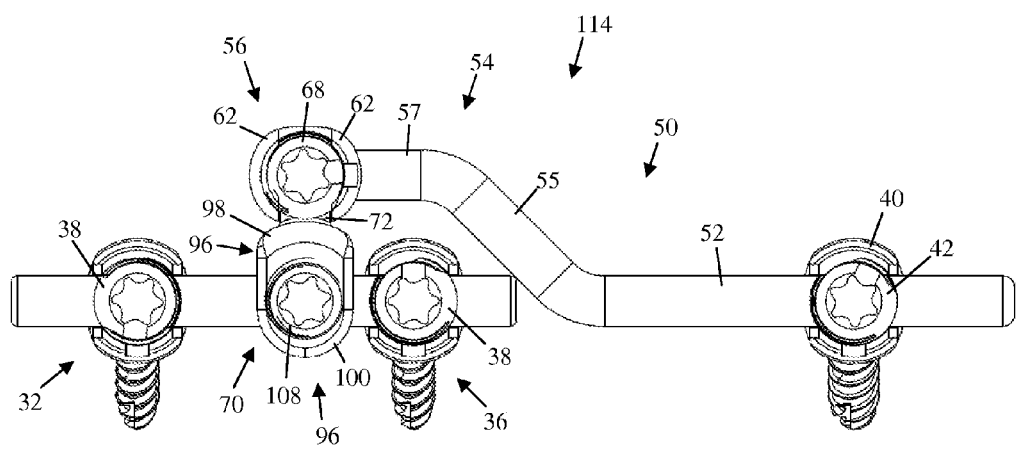
FIG. 19 is a top view of an extended spinal fixation construct with the extension rod of FIG. 10 and the connector of FIG. 13.
Figure 20:
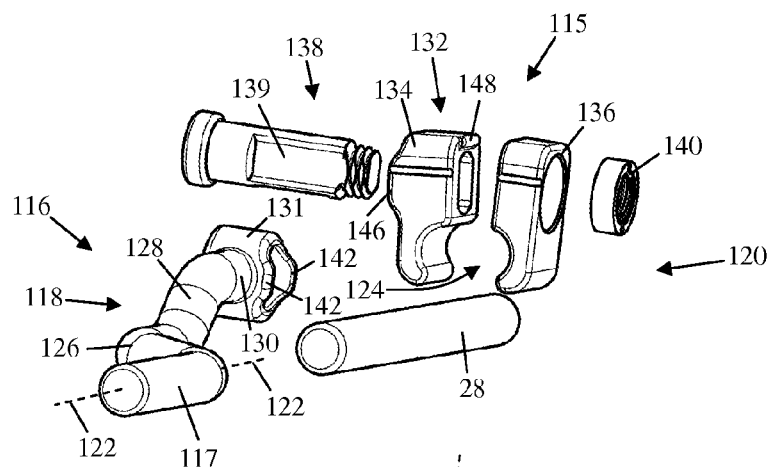
FIG. 20 is an exploded perspective view of an example embodiment of an extension rod for linking one or more pedicle screws to an existing spinal fixation construct, according to still another example embodiment.
Figure 21:
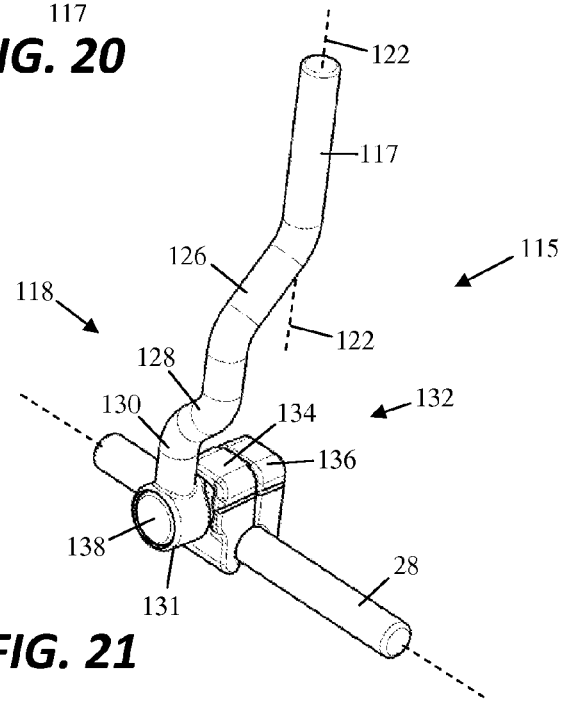
FIG. 21 is a perspective view of the extension rod of FIG. 20 depicting a lever arm in an open (unlocked) position, according to one example embodiment.
Figure 22:
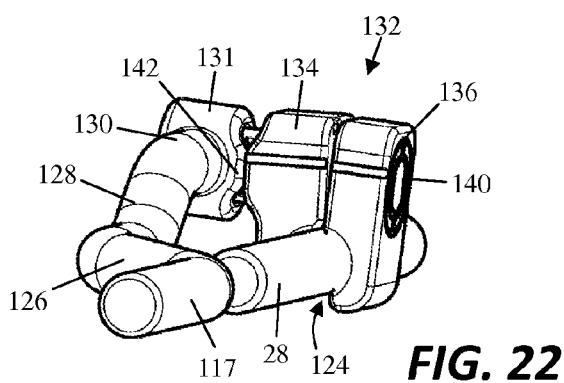
FIG. 22 is a perspective view of the extension rod of FIG. 20 depicting a lever arm in closed (locked) position, according to one example embodiment.

FIGS. 14-19 illustrate an extended (during a subsequent surgery) fixation construct (illustrated without the spine) constructed with the extension rod 50 and the example connectors 76, 86, and 96. FIGS. 14 and 15 depict isometric and top views of an extended fixation construct 110 using the extension rod 50 with the prophylactic tulip connector 76. FIGS. 16 and 17 depict isometric and top views of an extended fixation construct 112 using the extension rod 50 with the open top connector 86. FIGS. 18 and 19 depict isometric and top views of an extended fixation construct 114 using the extension rod 50 with the open side connector 96.

FIGS. 20-24 illustrate still another example embodiment of a fusion extension rod 115. The extension rod includes a lever arm 116 having an extension segment 117, an offset segment 118, and a connecting element 120. A longitudinal axis 122 extends along the extension segment 117 and through a rod slot 124 of the connecting element. At least the extension segment 117 is generally cylindrical and dimensioned to be received within a rod capturing component of the new pedicle screw(s) 40. The offset segment 118 can be further divided into three sub segments. The first sub segment 126 extends away from the extension segment 117 oblique to the longitudinal axis 122 in a horizontal plane. The second sub segment 128 extends away from the first sub segment 126 oblique to the longitudinal axis 122 in a vertical plane. The third sub segment 130 extends from the second sub segment along an axis generally parallel to the longitudinal axis. A coupling end 131 is formed at the end of the third sub segment. The lever arm 116 is movable from an open to a closed position as described below and the offset segment 118 is described relative to the closed position.

The connecting element 120 comprises a cam operated clamp 132 that can couple to a wide range of index rod diameters. The clamp 132 includes an active clamping block 134 and a static clamping block 136. Cutouts in each of the static clamping block 136 and active clamping block 134 together form rod slot 124. The active clamping block 134, static clamping block 136, and lever arm 116 are coupled together with a threaded pin 138 and nut 140, as best viewed in FIG. 20. The lever arm 116 rotates around the threaded pin 138 from an open position, illustrated in FIG. 21, in which the longitudinal axis 122 is oblique to the axis of the index rod 28 (and rod slot 124 of the clamp 132) to the closed position, illustrated in FIG. 22, in which the longitudinal axis 122 is coincident with the index rod (and rod slot 124). As the lever arm 116 rotates from the open position to the closed position ramps 142 on the edge of the coupling end 131 engage ramps 146 on the active clamping block 134 causing the active clamping block to translate along the threaded pin 138 towards the static clamping block 136. The nut 140 acts as a locking mechanism preventing translation of the static clamping block 136. Flats 139 on the threaded pin 138 prevent rotation of the active clamping block 134 about the axis of the pin as the lever arm 116 rotates about the pin. A pivot protrusion 148 situated near the top of the active clamping block 134 engages the static clamping block 132 causing the active clamping block 134 to pivot around the protrusion, increasing the clamping effect at the rod slot 124.

Figure 23:
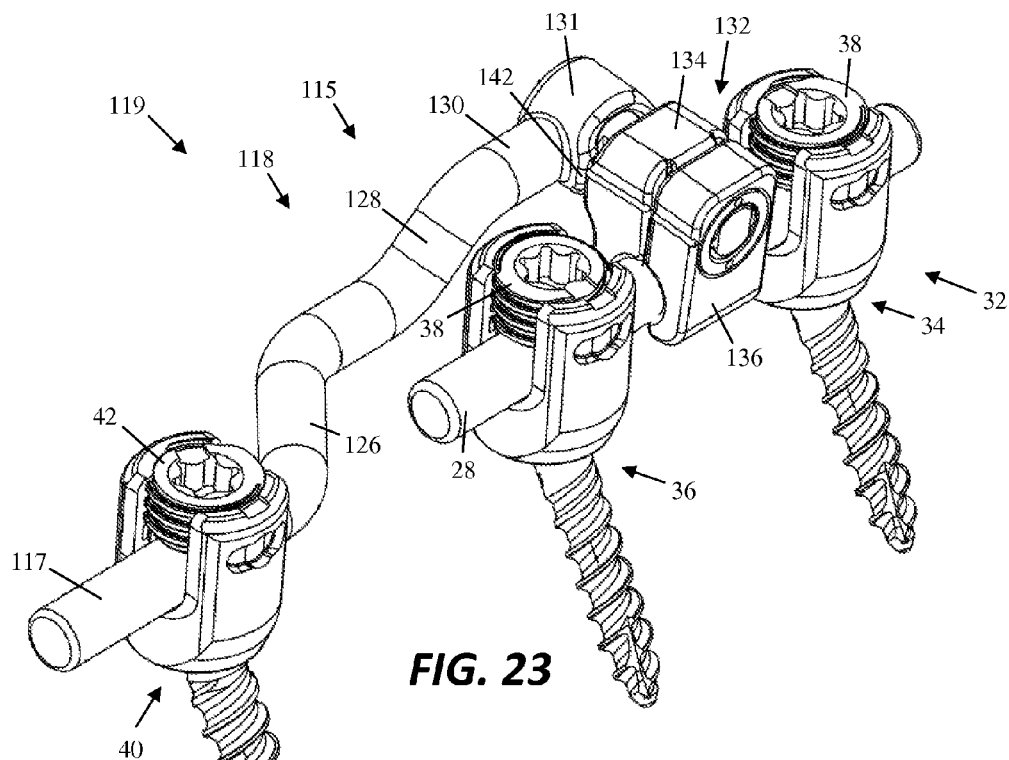
FIG. 23 is a perspective view of an extended spinal fixation construct with the extension rod of FIG. 20.
Figure 24:
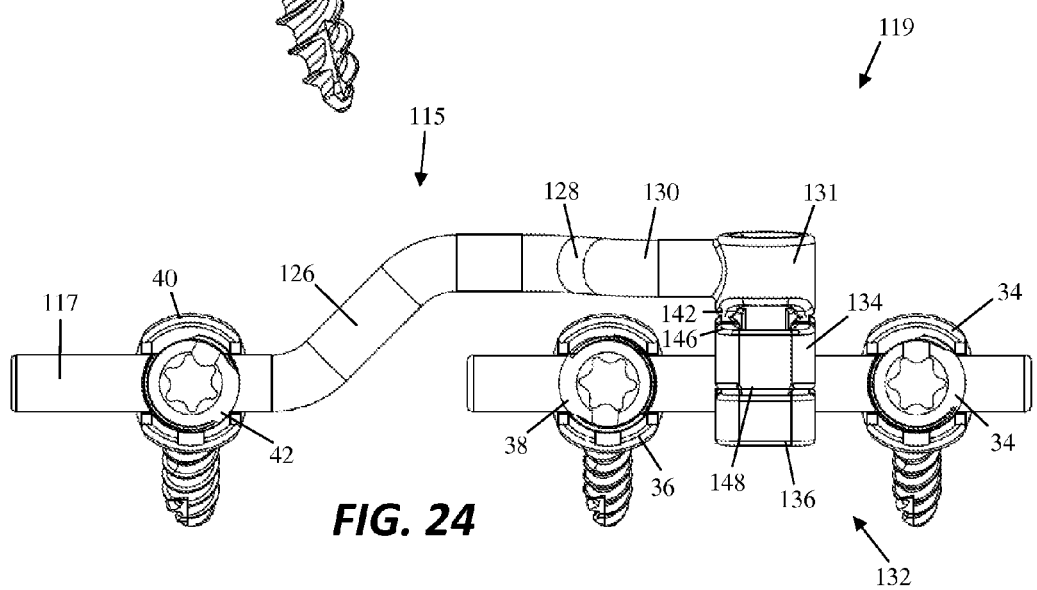
FIG. 24 is a top view of an extended spinal fixation construct with the extension rod of FIG. 20.

FIGS. 23 and 24 are isometric and top views of an extended (during a subsequent surgery) fixation construct (illustrated without the spine) 119 constructed with the extension rod 115. During the subsequent surgery at least a portion of the index rod 28 is exposed and the clamp is placed over the index rod with the lever arm 11 in the open position. The lever arm 116 is rotated to the closed position and clamping the index rod in the rod slot 124 while the extension segment 117 of the lever arm is fitted in and locked the new pedicle screw(s) 40.

Figure 25:
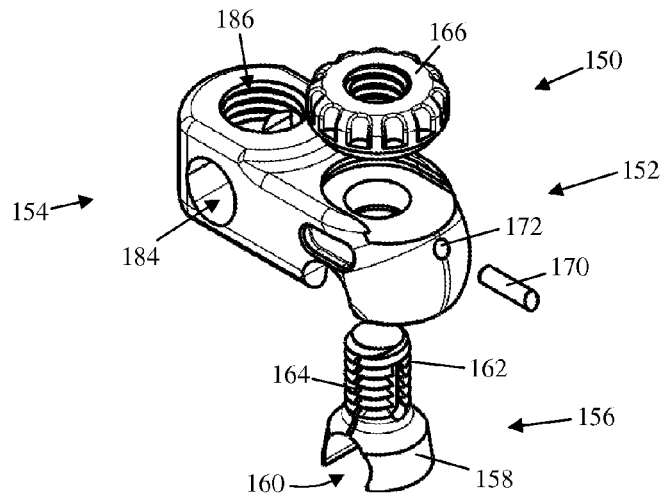
FIG. 25 is an exploded perspective view of an example embodiment of top loading connector for use with extension rod for linking one or more pedicle screws to an existing spinal fixation construct, according to one example embodiment.

FIGS. 25-31 illustrate example embodiments of a top loading (i.e. the connector couples to the rod from top down) rod-to-rod connector 150. According to one example, the rod-to-rod connector 150 can be utilized with a simple offset rod 151 (i.e. an offset rod with no connecting element, FIGS. 28-31) to extend a fixation construct during a subsequent surgery without requiring removal of any of the initial hardware. The top loading connector 150 accommodates a wide range of index rod 28 sizes employed in the spinal market. The rod-to-rod connector 150 is not limited to use for extending an existing fixation construct and may be used for other situations in which it is desirable to connect two rods together. The connector 150 includes at one end a primary top loading connection site 152 and at a second end a secondary connection site 154. FIG. 25 is an exploded view illustrating the workings of the top loading connection site 152. The connection is achieved via deformation of a collet 156 around the index rod 28. The collet 156 resides in a tapered collet housing and includes a rod gripper 158 defining a rod slot 160 and a threaded body 162 extending from the rod gripper. A slot 164 intersects the rod gripper and extends through a portion of the threaded body. A nut 166 threadedly engages the body 162 and when rotated in the appropriate direction draws the collet 156 into the collet housing, causing the deformation about the rod 28. Pin 170 extends through channel 172 to prevent rotation of the collet 156 when the nut is rotated.

Figure 26:
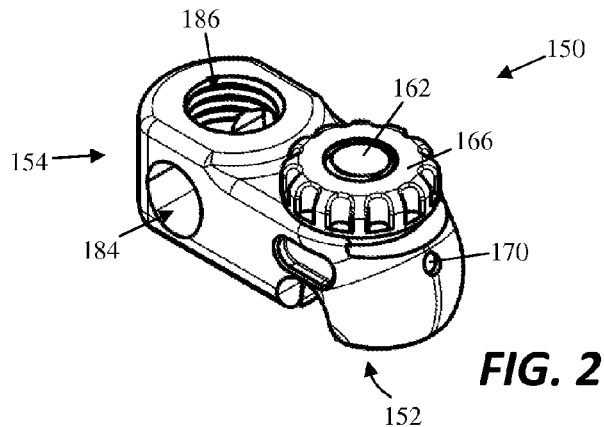
FIG. 26 is a perspective view of the top loading connector of FIG. 25, having a an closed secondary connection site, according to an example embodiment.
Figure 29:
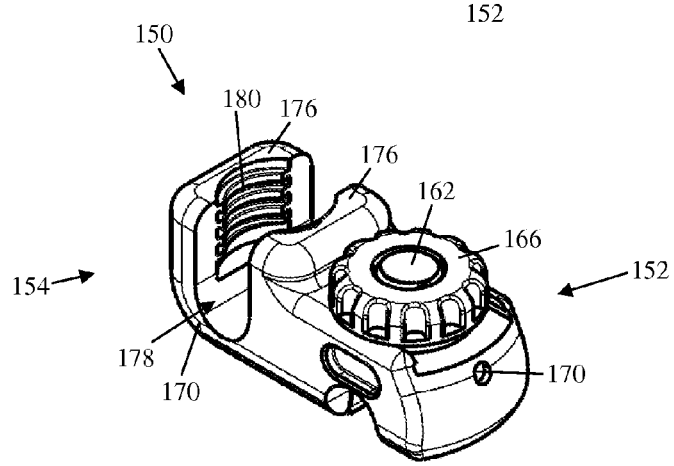
FIG. 29 is a perspective view of the top loading connector of FIG. 25, having a an open top secondary connection site, according to an example embodiment.
Figure 27:
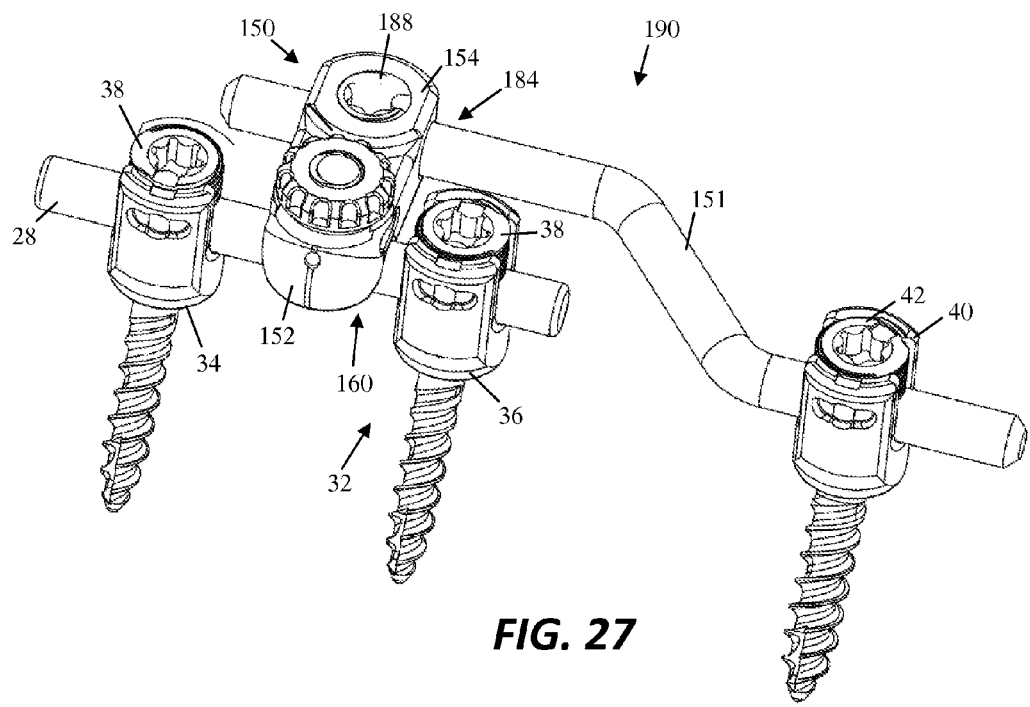
FIG. 27 is a perspective view of an extended spinal fixation construct with the connector of FIG. 26.
Figure 28:
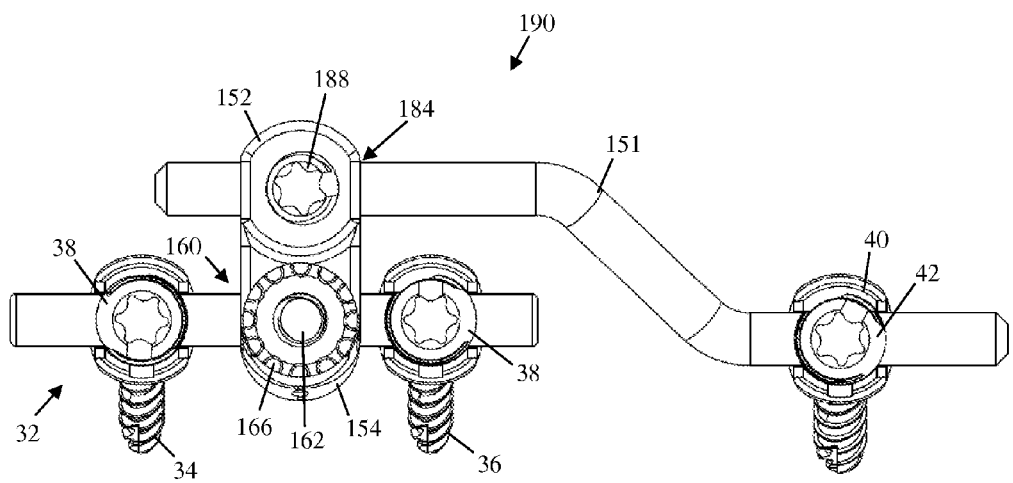
FIG. 28 is a top view of an extended spinal fixation construct with the connector of FIG. 26.
Figure 30:
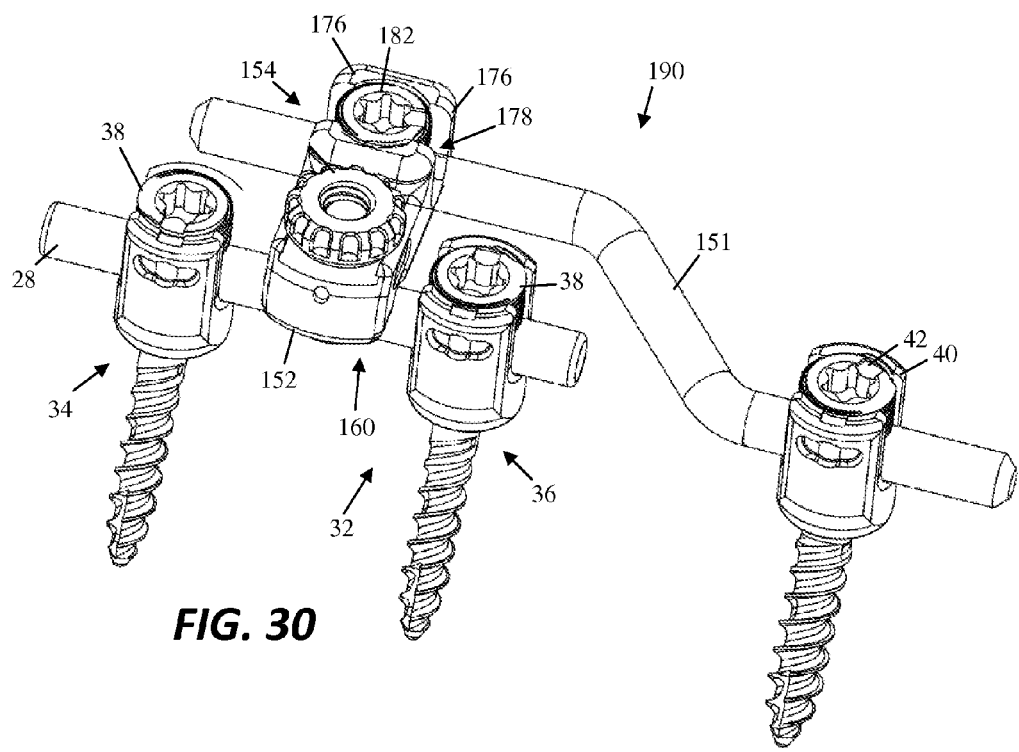
FIG. 30 is a perspective view of an extended spinal fixation construct with the connector of FIG. 29.
Figure 31:
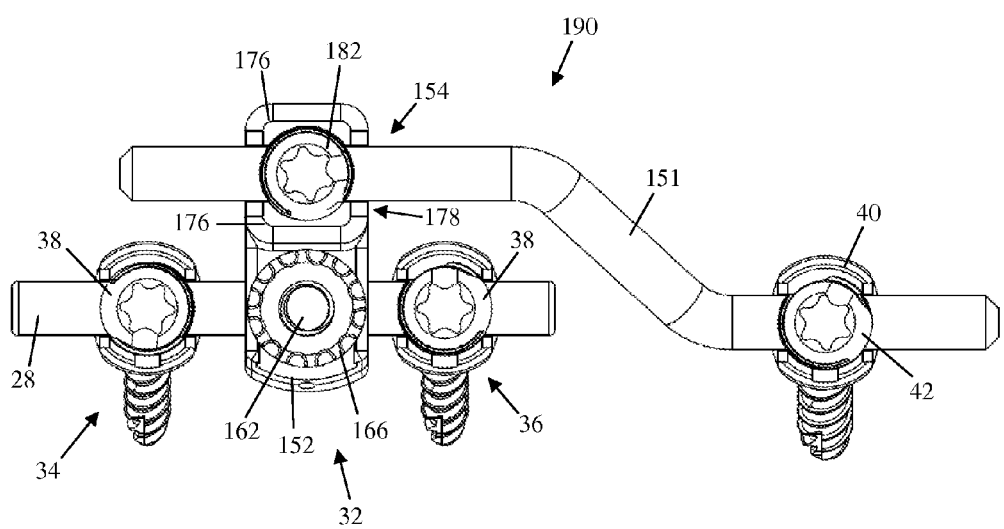
FIG. 31 is a top view of an extended spinal fixation construct with the connector of FIG. 29.

The secondary connection site 154 can be configured to utilize any number of known connection configurations. For example, FIGS. 29-31 illustrate an open top connector similar to the open top connector described with relation to FIG. 12 and the connector 86. By way of example, the top loading connector includes a base 174 with a pair of upstanding arms 176 extending therefrom and separated by rod capture slot 178. The arms 176 are equipped with a locking cap guide and advancement feature 180, such as by way of example, the helically wound flange feature disposed on the interior face of each arm 176. The guide and advancement feature 180 mates with a complementary guide and advancement feature formed on a locking cap 182 to lock the secondary connection site to the offset rod 151. By way of further example, FIGS. 26-28 illustrate a closed connector having a closed rod passage 184 with a locking cap guide and advancement feature, for example, threaded aperture 186 opening into the rod passage 184. The guide and advancement feature 186 mates with a complementary guide and advancement feature formed on a locking cap 188 to lock the secondary connection site to the offset rod 151.

FIGS. 27-28 and 30-31 illustrate an extended (during a subsequent surgery) fixation construct (illustrated without the spine) constructed with the rod-to-rod connector 150 and an extension rod 151. FIGS. 30-31 depict isometric and top views of an extended fixation construct 190 using an embodiment of the connector 150 having an open top secondary connection site. FIGS. 27-28 depict isometric and top views of the extended fixation construct 190 using an embodiment of the connector 150 having a closed connector secondary connection site. By way of example, during the subsequent surgery at least a portion of the index rod is exposed and the primary top loading connection site 152 is positioned over the rod 28 such that the rod rests in the rod slot 160. The nut 166 is then rotated to clamp the collet 156 against the index rod 28. The extension rod 151 is coupled to secondary connection site 154 at one end and to the new pedicle screw(s) 40 at the opposite end.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An extension rod for connecting to a preexisting fixation construct anchored to a spine during a previous surgery in order to extend the fixation construct to span at least one additional spinal level, the preexisting construct including at least two index pedicle screws and an index rod linking the index pedicle screws, the extension rod comprising:
   a lever arm, the lever arm including an extension segment having a longitudinal axis and adapted to be rigidly coupled to a pedicle screw, and an offset segment extending away from the extension segment oblique to the longitudinal axis; and
   a connecting element attached to the lever arm, the connecting element including a rod slot configured to receive a portion of the index rod of a preexisting fixation construct therein, wherein movement of the lever arm from a first position to a second position rigidly couples the extension rod to the index rod, and wherein moving the lever arm to the second position also aligns the longitudinal axis of the extension segment with a longitudinal axis of the index rod.

2. The extension rod of claim 1, wherein the connecting element includes a clamp.

3. The extension rod of claim 2, wherein the lever arm includes cam surfaces to operate the clamp.

4. The extension rod of claim 3, wherein the clamp includes an active clamping block and a static clamping block.

5. The extension rod of claim 2, wherein the rod slot opens in the bottom of the clamp such that the extension rod is top loading.

6. The extension rod of claim 5, wherein the offset segment includes a first portion that extends away from the extension segment oblique to the longitudinal axis in a horizontal plane and a second portion that extends away from the extension segment oblique to the longitudinal axis in a vertical plane.

7. The extension rod of claim 1, wherein the extension segment has a length configured to extend across multiple spinal levels.

* * * * *